US012636268B2

(12) United States Patent
Allegretti et al.

(10) Patent No.: US 12,636,268 B2
(45) Date of Patent: May 26, 2026

(54) CXCL8 INHIBITORS FOR USE IN THE TREATMENT OF COVID-19

(71) Applicant: Dompe' Farmaceutici SPA, Milan (IT)

(72) Inventors: Marcello Allegretti, L'Aquila (IT); Flavio Mantelli, L'Aquila (IT); Lorenzo Piemonti, Milan (IT)

(73) Assignee: Dompe' Farmaceutici SPA, Milan (IT)

( * ) Notice: Subject to any disclaimer, the term of this patent is extended or adjusted under 35 U.S.C. 154(b) by 810 days.

(21) Appl. No.: 17/914,529

(22) PCT Filed: Mar. 24, 2021

(86) PCT No.: PCT/EP2021/057624
§ 371 (c)(1),
(2) Date: Sep. 26, 2022

(87) PCT Pub. No.: WO2021/191305
PCT Pub. Date: Sep. 30, 2021

(65) Prior Publication Data

US 2023/0141355 A1 May 11, 2023

(30) Foreign Application Priority Data

Mar. 26, 2020 (EP) ..................................... 20166073
Dec. 2, 2020 (EP) ..................................... 20211370

(51) Int. Cl.

| | |
|---|---|
| ***A61K 31/18*** | (2006.01) |
| ***A61K 31/135*** | (2006.01) |
| ***A61K 31/167*** | (2006.01) |
| ***A61K 31/415*** | (2006.01) |
| ***A61K 31/431*** | (2006.01) |

(Continued)

(52) U.S. Cl.
CPC ............ *A61K 31/18* (2013.01); *A61K 31/135* (2013.01); *A61K 31/167* (2013.01); *A61K 31/415* (2013.01); *A61K 31/431* (2013.01); *A61K 31/496* (2013.01); *A61K 31/546* (2013.01); *A61K 31/573* (2013.01); *A61K 31/616* (2013.01); *A61K 31/635* (2013.01); *A61K 31/675* (2013.01); *A61K 31/7052* (2013.01);

(Continued)

(58) Field of Classification Search
CPC .............. A61K 2300/00; A61K 31/135; A61K 31/167; A61K 31/18; A61K 31/415; A61K 31/426; A61K 31/431; A61K 31/496; A61K 31/546; A61K 31/573; A61K 31/616; A61K 31/635; A61K 31/675; A61K 31/7052; A61K 31/706; A61K 31/727; A61K 31/737; A61K 38/2006; A61K 45/06; A61P 11/00; A61P 31/14

See application file for complete search history.

(56) References Cited

FOREIGN PATENT DOCUMENTS

| | | | |
|---|---|---|---|
| CN | 1449285 | A | 10/2003 |
| CN | 101448784 | A | 6/2009 |

(Continued)

OTHER PUBLICATIONS

Daga et al (journal of Advanced research in Medicine, vol. 6, issue Apr. 2019, pp. 1-9) (Year: 2019).*

(Continued)

*Primary Examiner* — Savitha M Rao
(74) *Attorney, Agent, or Firm* — Clark & Elbing LLP

(57) ABSTRACT

The present invention relates to CXCL8 inhibitors for use in the treatment of COVID-19 patients with pneumonia.

16 Claims, 1 Drawing Sheet

(51) Int. Cl.

| | |
|---|---|
| ***A61K 31/496*** | (2006.01) |
| ***A61K 31/546*** | (2006.01) |
| ***A61K 31/573*** | (2006.01) |
| ***A61K 31/616*** | (2006.01) |
| ***A61K 31/635*** | (2006.01) |
| ***A61K 31/675*** | (2006.01) |
| ***A61K 31/7052*** | (2006.01) |
| ***A61K 31/737*** | (2006.01) |
| ***A61K 38/20*** | (2006.01) |
| ***A61P 31/14*** | (2006.01) |

(52) U.S. Cl.

CPC ........ *A61K 31/737* (2013.01); *A61K 38/2006* (2013.01); *A61P 31/14* (2018.01)

(56) References Cited

FOREIGN PATENT DOCUMENTS

| | | | | |
|---|---|---|---|---|
| CN | 102656140 A | | 9/2012 | |
| CN | 110769824 A | | 2/2020 | |
| CN | 111378008 A | | 7/2020 | |
| CN | 111701015 A | | 9/2020 | |
| EP | 2316820 A1 | | 5/2011 | |
| EP | 3409277 A1 | | 12/2018 | |
| RU | 2375347 C2 | | 12/2009 | |
| WO | WO-02/05814 A1 | | 1/2002 | |
| WO | WO-2005/090295 A2 | | 9/2005 | |
| WO | WO-2007/135080 A2 | | 11/2007 | |
| WO | WO-2010/031835 A2 | | 3/2010 | |
| WO | WO-2010/126748 A1 | | 11/2010 | |
| WO | WO-2018219865 A1 | * | 12/2018 | .............. A61P 31/04 |
| WO | WO-2020/241759 A1 | | 12/2020 | |

OTHER PUBLICATIONS

Search Report dated Oct. 14, 2024 for Chinese Patent Application No. 202180024025.3, Allegretti et al., "CXCL8 inhibitors for treatment of COVID-19," filed Mar. 24, 2021 (3 pages).

Office Action dated May 31, 2024, for Russian Patent Application No. 2022127466, Allegretti et al., "CXCL8 Inhibitors for Use in the Treatment of COVID-19," filed Mar. 24, 2021 (partial English translation) (18 pages).

Anonymous: "Reparixin in COVID-19 Pneumonia—Efficacy and Safety," U.S. National Library of Medicine, ClinicalTrials.gov, <https://clinicaltrials.gov/ct2/show/NCT04794803>, dated Mar. 12, 2021, retrieved Nov. 1, 2022 (11 pages).

Anonymous: Agenzia Italiana del Farmaco, "Modulo di Comunicazione al Richiedente, Agli Altri Comitati Etici ad Aifa della Decisione del Comitato Etico Relativa al Parere Unico," <https://www.dompe.us/media/press-releases/aifa-announces-italian-authorization-of-phase-2-3-clinical-trial-of-domp%C3%A9s-reparixin-for-the-treatment-of-severe-patients-with-covid-19-pneumonia>, dated Apr. 24, 2020, retrieved Nov. 1, 2022 (7 pages).

Alkotaji, "Azithromycin and ambroxol as potential pharmacotherapy for SARS-CoV-2," Int. J. Antimicrob. Agents 56(6):106192 (Dec. 2020) (4 pages).

Chen et al., "The coronavirus diseases 2019 (COVID-19) pneumonia with spontaneous pneumothorax: a case report," BMC Infect. Dis. 20(1):662 (Sep. 9, 2020) (5 pages).

Dompé, "AIFA Announces Italian Authorization of Phase 2/3 Clinical Trial of Dompé's Reparixin for the Treatment of Severe Patients with COVID-19 Pneumonia," <https://www.dompe.us/media/press-releases/aifa-announces-italian-authorization-of-phase-2-3-clinical-trial-of-domp%C3%A9s-reparixin-for-the-treatment-of-severe-patients-with-covid-19-pneumonia>, dated May 12, 2020, retrieved Nov. 1, 2022 (3 pages).

Dompé, "Clinical Study Protocol: Adaptive phase 2/3, randomized, controlled multicenter study on the efficacy and safety of Reparixin in the treatment of hospitalized patients with COVID-19 pneumonia," <https://www.dompe.us/media/press-releases/aifa-announces-italian-authorization-of-phase-2-3-clinical-trial-of-domp%C3%A9s-reparixin-for-the-treatment-of-severe-patients-with-covid-19-pneumonia>, Version n. 1.5, dated Apr. 23, 2020, retrieved Nov. 1, 2022 (51 pages).

Hoffmann et al., "Nafamostat Mesylate Blocks Activation of SARS-CoV-2: New Treatment Option for COVID-19," Antimicrob. Agents Chemother. 64(6):e00754-20 (Apr. 2020) (3 pages).

Hoffmann et al., "SARS-CoV-2 Cell Entry Depends on ACE2 and TMPRSS2 and Is Blocked by a Clinically Proven Protease Inhibitor," Cell 181(2):271-280 (Apr. 16, 2020).

International Search Report and Written Opinion mailed Jun. 24, 2021, for PCT International Application No. PCT/EP2021/057624, Allegretti et al., "CXCL8 Inhibitors for use in the Treatment of COVID-19," filed Mar. 24, 2021 (20 pages).

Jafari et al., "Large saddle pulmonary embolism in a woman infected by COVID-19 pneumonia," Eur. Heart J. 41(22):2133 (May 6, 2020) (1 page).

Martinez, "Compounds with therapeutic potential against novel respiratory 2019 coronavirus," Antimicrob. Agents Chemother. 64(5):e00399-20 (Mar. 9, 2020) (7 pages).

Qin et al., "Dysregulation of Immune Response in Patients with Coronavirus 2019 (COVID-19) in Wuhan, China," Clin. Infect. Dis. 71(15):762-768 (Jul. 28, 2020).

Wang et al., "Remdesivir and chloroquine effectively inhibit the recently emerged novel coronavirus (2019-nCoV) in vitro," Cell Res. 30(3):269-271 (Feb. 2020).

Zarbock et al., "Therapeutic inhibition of CXCR2 by Reparixin attenuates acute lung injury in mice," Br. J. Pharmacol. 155(3):357-364 (2008).

Bankov et al., "The Way of SARS-CoV-2 Pneumonia—An Early-Pandemic Review of the Key Manifestations and Severity." J. Clin. Med. 2025, 14: 7096, pp. 1-13 (Oct. 2025) (13 pages).

Menezes et al., "SARS-CoV-2 pneumonia—receptor binding and lung immunopathology: a narrative review." Crit Care, 2021, 25:53, pp. 1-13 (Feb. 2021) (13 pages).

* cited by examiner

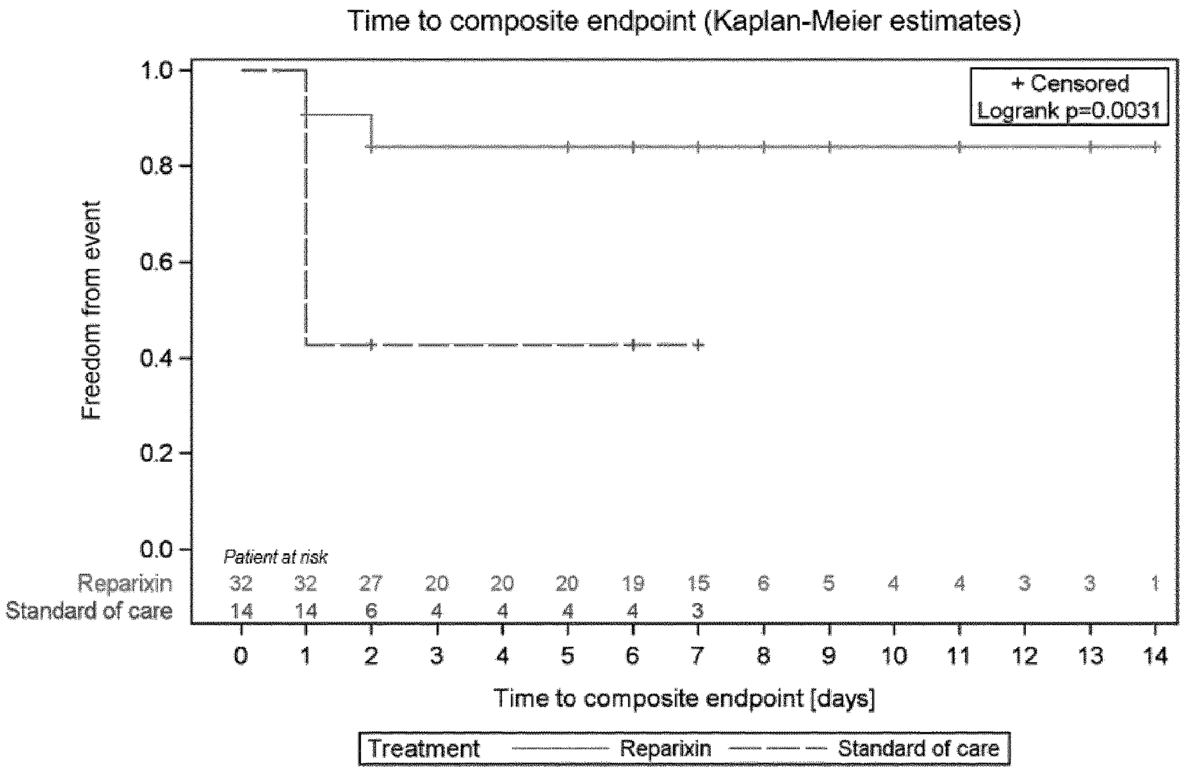
Time to composite endpoint (Kaplan-Meier estimates)
+ Censored
Logrank p=0.0031
Freedom from event
1.0
0.8
0.6
0.4
0.2
0.0
Patient at risk
Reparixin 32 32 27 20 20 20 19 15 6 5 4 4 3 3 1
Standard of care 14 14 6 4 4 4 4 3
0 1 2 3 4 5 6 7 8 9 10 11 12 13 14
Time to composite endpoint [days]
Treatment Reparixin Standard of care

CXCL8 INHIBITORS FOR USE IN THE TREATMENT OF COVID-19

FIELD OF THE INVENTION

The present invention relates to compounds for the treatment of COVID-19, in particular for use in the improvement of respiratory function in patients affected by pneumonia caused by SARS-CoV-2.

STATE OF THE ART

Coronaviruses (Covs) are a large family of viruses belonging to the family Coronaviridae and are enveloped, positive-sense RNA viruses. The limited number of coronaviruses known to be circulating in humans were considered to cause mild infections and they were regarded in the past as relatively harmless respiratory human pathogens. However, in the last years the emergence of the Severe Acute Respiratory Syndrome Coronavirus (SARS-CoV) and the Middle East Respiratory Syndrome (MERS) virus revealed that some coronaviruses can cause severe and sometimes fatal respiratory tract infections in humans (Pereira, H et al., 1989 Coronaviridae. Andrewes 'Viruses of Vertebrates, 5th ed.pp. 42-57; Holmes, K. V. et al., Virology 1996,1: 1075-1093).

In December 2019, atypical pneumonia cases that were identified to be caused by a new coronavirus emerged in Wuhan, China, and later rapidly spread worldwide. The World Health Organization officially named the new disease as "COVID-19", while the International Committee on Taxonomy of Viruses named the new virus as "SARS-CoV-2".

The symptoms of human infection with SARS-CoV-2 are generally fever, fatigue, dry cough and dyspnea. Investigations of the epidemiological and clinical characteristics and outcomes of patients infected by SARS-CoV-2 demonstrated that the infection causes a pneumonia similar to the known SARS-CoV pneumonia with impairment of respiratory function. Noteworthy, a considerable percentage of COVID-19 pneumonia cases progresses to severe and critical types, among which acute lung injury (ALI) and acute respiratory distress syndrome (ARDS) are the most common complications, resulting in a large number of hospitalized patients who require supplemental oxygen, mechanical ventilation, or even Extra Corporeal Membrane Oxygenation (ECMO).

It is believed that, in case of coronaviruses, direct cytopathic effects and viral evasion of host immune responses play major roles in disease severity (Min et al, Sci Rep 2016; 6: 25359; Channappanavar et al, Semin Immunopathol 2017, 39(5): 529-539).

In a recent study (Chuan Qin et al, Clin Infect Dis, 2020, doi: 10.1093/cid/ciaa248) wherein laboratory parameters of severe COVID-19 patients with respiratory distress and low oxygen saturation were compared with those of patients with milder forms, it has been reported that severe COVID-19 patients show a dysregulation of the immune response, with a pronounced lymphocytopenia. Furthermore, in severe patients also higher serum levels of pro-inflammatory cytokines, such as TNF-α, IL-1 and IL-6, and chemokines, such as IL-8 were observed.

From the above data, it can be can be concluded that in severe COVID-19 pneumonia patients, the immune system is dysregulated, resulting in impairment of the defense mechanisms against the virus, extensive infection of the lungs, and associated inflammatory response, with the production of a cytokine storm which worsens the tissue damage caused by the virus.

A further factor that has been suggested to exacerbate the severity of the respiratory impairment in COVID-19 patients seems to be the exposure to air pollution, in particular to particulate matter.

A positive correlation has been demonstrated between exposure to particulate matter, in particular to $PM_{10}$ levels, and increased risk of death in patients with SARS-CoV infection (Yan Cui et al, Environmental Health 2003, 2(1): 15). From preliminary data, the same correlation seems to exist with SARS-CoV-2 infections, where the number of severe cases is concentrated in areas with high levels of $PM_{10}$.

Particulate matter has been shown to cause damage and fibrosis in the lungs and to increase the susceptibility to different pathogens, including viruses, thus increasing risk and severity of respiratory infections (Liyao Yang, 2020, Front Cell Dev Biol 8, 91; I-Yin Cheng et al, Int J Mol. Sci., 2020, 21, 227; Horne et al, Am J Respir Crit Care Med, 2018, 198(6), 759).

At the moment, the clinical management of COVID-19 pneumonia includes co-infection prevention and supportive care for respiratory distress, including supplementary oxygen and mechanical ventilatory support when indicated.

It is therefore strongly felt the need of identifying an effective therapeutic approach for this disease, in particular for the improvement of respiratory function, which is heavily impaired in severe patients and consists in the most critical event of the disease that can lead patients to death.

A large number of drugs are currently being tested in clinical trials on COVID-19 patients worldwide.

Compounds that act by inhibiting neutrophil recruitment, such as CXCL8 inhibitors, have been suggested as potential therapeutic approaches in Acute Lung Injury. In particular, the therapeutic potential of CXCL8 inhibitor reparixin was studied in murine models of LPS-induced pulmonary inflammation and acid-induced ALI (Zambrock et al, Br J Pharmacol 2008; 155:357-364).

However, the above work suggests that treatment with reparixin may be beneficial only in the first, non bacterial phases of ALI since neutrophils are in the first line in host defence against pathogens, and the impairment of neutrophil recruitment may have deleterious effects in the presence of an infection (Zarbock et al, Br J Pharmacol 2008, 155: 357-364; Moore et al., J Immunol. 2000, 164: 908-915). This aspect is particularly critical in COVID-19 patients in view of the observed dysregulation of the immune system.

The biological activity of CXCL8 is mediated by the interaction with two receptors, CXCR1 and CXCR2. CXCR1 is selective for CXCL8, whereas CXCR2 is a promiscuous receptor, binding a number of different cytokines and chemokines such as CXCL1, CXCL2, CXCL3, CXCL5, CXCL6, and CXCL7 (Baggiolini, M., (2000) Immunol. Rev. 177, 5-7).

SUMMARY OF THE INVENTION

The present inventors have now surprisingly found that administration of a CXCL8 inhibitor, such as reparixin, to COVID-19 patients with pneumonia is able to improve respiratory function, measured as partial arterial oxygen pressure (PaO2) to fraction of inspiration O2 (FiO2) ratio.

Furthermore, the present inventors have found that the administration of a CXCL8 inhibitor, such as reparixin, to COVID-19 patients with severe pneumonia is more effective in preventing the progression to more severe respiratory disease compared to standard of care treatment alone. In fact, these patients are characterised by fewer days of oxygen use and shorter duration of mechanical ventilation, compared to those treated only with the standard of care treatment. Furthermore, treatment with a CXCL8 inhibitor results in a reduced time of recovery of the patients.

Accordingly, a first object of the present invention is a CXCL8 inhibitor for use in the treatment of patients with COVID-19 pneumonia.

A second object of the invention is a pharmaceutical composition comprising i) a CXCL8 inhibitor and ii) at least one inert pharmaceutically acceptable excipient, for use in the treatment of patients with COVID-19 pneumonia.

A third object of the invention is a method of treating COVID-19 pneumonia, comprising administering to a patient affected thereby a CXCL8 inhibitor.

FIGURES

FIG. 1 shows the freedom from a composite event (at least one of the following events: death, supplemental oxygen requirement, invasive mechanical ventilation use, admission to ICU, and use of a rescue medication for any reason), measured as percentage expressed in decimal form, over time for the Reparixin group and Control group, as described in Example 1. The numbers at the bottom of the figures, in correspondence of Reparixin and Standard of Care, indicate the number of patients at risk evaluated at each timepoint for the Reparixin group and Control group, respectively.

DETAILED DESCRIPTION OF THE INVENTION

A first object of the present invention is a CXCL8 inhibitor for use in the treatment of patients with COVID-19 pneumonia.

According to the present invention, by "COVID-19 pneumonia" it is meant an inflammatory condition of the lung associated to a SARS-CoV-2 infection. This is a severe complication of COVID-19 affecting a percentage of the patients.

Preferably, said CXCL8 inhibitor for use in the treatment of patients with COVID-19 pneumonia is administered in combination with a standard of care treatment for COVID-19 patients.

According to the present invention, by "standard of care treatment for COVID-19 patients." it is meant a pharmacological treatment that includes one or more drugs that have been approved by regulatory authorities i) as a treatment for COVID-19 or ii) as a treatment for other pathological conditions and symptoms thereof and that are used in clinical practice as a treatment of symptoms and complications that are associated to COVID-19.

Preferably, said standard of care treatment consists in the treatment of the patient with at least one drug selected from:

i) antiviral drugs, preferably remdesivir;
ii) antipyretic, analgesic and antiinflammatory drugs, preferably non-steroidal anti-inflammatory drugs, corticosteroids, cytokine, chemokine and interleukin inhibitors, more preferably selected from dexhamethasone, paracetamol, anakinra, celecoxib, prednisone, prednisolone, methylprednisolone, piryrone, and tramadol;
iii) antibiotics, preferably selected from piperacillin in association with tazobactam, azithromycin and ceftriazone; and
iv) anti-coagulants and antithrombotic drugs, preferably selected from enoxaparin and acetylsalicylic acid.

Preferably, said CXCL8 inhibitor is for use in improving respiratory function in said patients, wherein said respiratory function is measured as partial arterial oxygen pressure (PaO2) to fraction of inspiration O2 (FiO2) ratio.

Preferably, the above patients have an impaired respiratory function.

In one embodiment, preferably said patients have values of partial arterial oxygen pressure (PaO2) to fraction of inspiration O2 (FiO2) ratio before the treatment of the invention below 400 mmHg, more preferably below 300 mmHg, below 200 mmHg or below 100 mmHg (wherein 1 mmHg=0.133 kPa). More preferably, said patients have values of partial arterial oxygen pressure (PaO2) to fraction of inspiration O2 (FiO2) ratio between 100 and 300 mmHg.

In another embodiment, also in combination with the previous embodiment, the patients have respiratory distress, with a respiratory rate of or above 30 breaths/min without oxygen supplementation.

Preferably, said improving respiratory function in said patients comprises increasing partial arterial oxygen pressure (PaO2) to fraction of inspiration O2 (FiO2) ratio of at least 20%, 50%, 80%, 100%, 120%, 150%, 200% or 250% in comparison with the ratio before treatment.

Preferably said improving respiratory function in said patients comprises increasing partial arterial oxygen pressure (PaO2) to fraction of inspiration O2 (FiO2) ratio to a value above 400 mmHg.

Preferably, said patients with COVID-19 pneumonia have lymphocytopenia.

According to a preferred embodiment, said patients with lymphocytopenia are adult patients (14 years and above) and have blood concentration of lymphocytes below 1000, below 900, below 850, below 800 or below 750 cells/microliter.

According to another preferred embodiment, said patients with lymphocytopenia are children (below 14 years of age) and have blood concentration of lymphocytes below 3000, below 2800, below 2500, below 2300 or below 2000 cells/microliter.

In one embodiment, said improving respiratory function in said patients means decreasing, delaying the onset of or preventing the need of supplemental oxygen requirement, mechanical ventilation use or admission to Intensive Care Unit.

Preferably, said patients with COVID-19 pneumonia have been exposed to $PM_{10}$ levels higher than 50 $\mu g/m^3$ for more than 20 days, preferably more than 30 days, even more preferably for 35 days in the year prior to SARS-CoV-2 infection. According to the present invention, the term $PM_{10}$ refers to the mass of particles present in the air having a 50% cutoff for particles with an aerodynamic diameter of 10 microns.

Preferably, said CXCL8 inhibitor is for use in reducing the time of clinical recovery of said patients. According to the present invention, by time of "clinical recovery" it is meant the period of time from the onset to the resolution of symptoms.

The term "CXCL8 inhibitor" according to the present application refers to any compound able to inhibit, partially or totally, the biological activity of CXCL8. Such a compound can act by decreasing the expression of CXCL8 or of its receptor(s) or by inhibiting the triggering of the intracellular signaling activated by the CXCL8 receptor(s). It is preferred that said CXCL8 activity inhibitor is able to inhibit at least 60%, preferably at least 70%, more preferably at least 80%, even more preferably at least 90% of PMN chemotaxis induced by an optimal concentration of CXCL8 (1 nM) at a concentration equal or below 500 nM, preferably below 100 nM.

According to a preferred embodiment, the CXCL8 inhibitor according to the present invention inhibits the activity of CXCL8 mediated by CXCR1 receptor or mediated by both CXCR1 and CXCR2 receptors. Preferably, according to this embodiment, said CXCL8 inhibitor is a CXCL8 receptor(s) inhibitor, which inhibits binding of CXCL8 to its receptor(s) and/or the intracellular signaling activated by the binding of CXCL8 to its receptor(s). Preferably, said CXCL8 receptor inhibitor is either an allosteric inhibitor or an orthosteric antagonist of CXCR1 receptor or of both CXCR1 and CXCR2 receptors. More preferably, the CXCL8 receptor(s) inhibitor according to the invention has an $IC_{50}$ value towards CXCR1 receptor in the low nanomolar range, preferably in the range 0.02-5 nanomolar.

Preferably, said CXCL8 inhibitor is selected from small molecular weight molecules, peptides and antibodies, more preferably it is a small molecular weight molecule. CXCL8 inhibitors according to the above definition, able to inhibit the activity of CXCL8 mediated by CXCR1 receptor or mediated by both CXCR1 and CXCR2 receptors, are well known in the art.

To date, several CXCL8 inhibitors, such as small molecules, peptides and antibodies, have been disclosed, many of which are currently undergoing clinical trials or are used in therapy. (Jie Jack, Expert Opinion Ther. Patents, 2001, 11(12), Chao J. et al., Bioorganic & Medicinal Chemistry Letters 17, 2007, p. 3778-3783, Busch-Petersen J. Current Topics in Medicinal Chemistry, 2006, 6, p. 1345-135, Allegretti et al, Immunology Letters 2012, Vol. 145, p. 68-78).

Preferred CXCL8 inhibitors according to the present invention are disclosed in WO2000/024710A1 and WO2005/090295, that also discloses their method of synthesis, their activity as CXCL8 inhibitors as well as their use as inhibitors of neutrophils chemotaxis and degranulation induced by CXCL8, and in the treatment of CXCL8-dependent pathologies.

Among these, CXCL8 inhibitors particularly preferred in the present invention are those of the following formula (I):

(I)

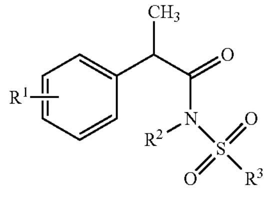

wherein $R^1$ is selected from a linear or branched $C_1$-$C_6$ alkyl, benzoyl, phenoxy, and trifluoromethanesulfonyloxy;

$R^2$ is selected from hydrogen atom and linear or branched $C_1$-$C_3$ alkyl; and $R^3$ is a linear or branched $C_1$-$C_6$ alkyl or trifluoromethyl, or a pharmaceutically acceptable salt thereof.

Preferably, $R^1$ is selected from benzoyl, isobutyl, and trifluoromethanesulfonyloxy. More in particular, $R^1$ is preferably linked to the phenyl ring in 3- or 4-position. According to the most preferred embodiment, $R^1$ is 3-benzoyl, 4-isobutyl or 4-trifluoromethanesulfonyloxy. Preferably, $R^2$ is selected from hydrogen atom or methyl.

Preferably, $R^3$ is selected from linear or branched $C_1$-$C_6$ alkyl, more preferably from linear of branched $C_1$-$C_3$ alkyl. According to the most preferred embodiment, $R^3$ is methyl.

Preferably, the chiral carbon of the compounds of formula (I) is in the RS or R configuration, more preferably it is in the R configuration.

Particularly preferred among said CXCL8 inhibitors of formula (I) are:

2-(4-isobutylphenyl)propionyl methansulfonamide, preferably R-(-)-2-(4-isobutylphenyl)propionyl methansulfonamide and pharmaceutically acceptable salts thereof, preferably the lysine salt thereof (also known as reparixin), and 2-(4-trifluoromethanesulfonyloxy)phenyl]-N-methanesulfonyl propionamide, preferably R(-)-2-(4-trifluoromethanesulfonyloxy)phenyl]-N-methanesulfonyl propionamide (and pharmaceutically acceptable salts thereof, in particular the sodium salt (also known as ladarixin) thereof.

Also, other preferred CXCL8 inhibitors according to the present invention are those disclosed in WO2010/031835, that also disclose their method of synthesis, their activity as CXCL8 inhibitors as well as their use as inhibitors of neutrophils chemotaxis and degranulation induced by CXCL8 and in the treatment of CXCL8 dependent pathologies. Among these, CXCL8 inhibitors particularly preferred in the present invention are those of the following formula (II):

(II)

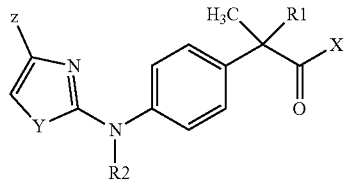

and pharmaceutically acceptable salts thereof, wherein:

R1 is hydrogen;

X is OH;

R2 is hydrogen or linear $C_1$-$C_4$ alkyl,

Y is a heteroatom selected from S, O and N,

Z is selected from linear or branched $C_1$-$C_4$ alkyl, linear or branched $C_1$-$C_4$ alkoxy, halo $C_1$-$C_3$ alkyl and halo $C_1$-$C_3$ alkoxy.

Preferably, the chiral carbon of the compounds of formula (II) is in the is in the RS or S configuration, more preferably in the S configuration.

Particularly preferred among said CXCL8 inhibitors of formula (II) is 2-(4-{[4-(trifluoromethyl)-1,3-thiazol-2-yl] amino}phenyl) propanoic acid, preferably (2S)-2-(4-{[4-(trifluoromethyl)-1,3-thiazol-2-yl]amino}phenyl) propanoic acid and pharmaceutically acceptable salts thereof, preferably the sodium salt thereof.

According to an alternative embodiment, the CXCL8 inhibitor according to the present invention inhibits the activity of CXCL8 mediated by CXCR2 receptor. Preferably, according to this embodiment, said CXCL8 inhibitor is a CXCL8 receptor(s) inhibitor, which inhibits binding of CXCL8 to CXCR2 receptor and/or the intracellular signaling activated by the binding of CXCL8 CXCR2 receptor. Preferably, said CXCL8 receptor inhibitor is either an allosteric inhibitor or an orthosteric antagonist of CXCR2 receptor. More preferably, the CXCL8 receptor(s) inhibitor according to the invention has an $IC_{50}$ value towards CXCR2 receptor in the low nanomolar range, preferably in the range 0.02-5 nanomolar.

Preferred CXCL8 inhibitors according to this embodiment are those disclosed in WO2007135080.

Among these, CXCL8 inhibitors particularly preferred in the present invention are those of the following formula (III):

(III)

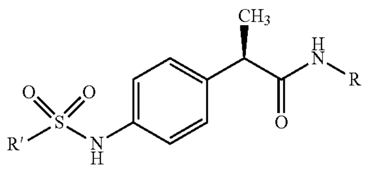

and pharmaceutically acceptable salts thereof, wherein:

R is selected from

H, OH, $C_1$-$C_5$-alkyl, $C_3$-$C_6$-cycloalkyl, $C_2$-$C_5$-alkenyl, $C_1$-$C_5$-alkoxy and phenyl, a heteroaryl group selected from unsubstituted pyrrole, tiophene, furane, indole, imidazole, thiazole, oxazole, pyridine and pyrimidine, a residue of formula CH2CH2O(CH2CH2)nR", wherein R" is H or $C_1$-$C_5$ alkyl and n is an integer from 0 to 2;

R' is selected from linear or branched $C_1$-$C_5$-alkyl, $C_3$-$C_6$-cycloalkyl, $C_2$-$C_5$-alkenyl and trifluoromethyl;

phenyl unsubstituted or substituted with a group selected from halogen, $C_1$-$C_4$ alkyl, $C_1$-$C_4$ alkoxy, trifluoromethyl;

unsubstituted benzyl;

an heteroaryl group selected from unsubstituted pyridine, pirimidine, pyrrole, thiophene, furane, indole, thiazole and oxazole.

Particularly preferred among said CXCL8 inhibitors of formula (III) is 2-{4[(isopropylsulfonyl)amino]phenyl}propanamide, preferably (2R)-2-{4[(isopropylsulfonyl)amino]phenyl}propanamide, and pharmaceutically acceptable salts thereof, preferably the sodium salt thereof.

The most preferred CXCL8 inhibitors according to the present invention are 2-(4-isobutylphenyl)propionyl methansulfonamide, preferably R-(-)-2-(4-isobutylphenyl)propionyl methansulfonamide and pharmaceutically acceptable salts thereof, preferably the lysine salt thereof.

According to a preferred embodiment, when the CXCL8 inhibitor is R-(-)-2-(4-isobutylphenyl)propionyl methansulfonamide, it is administered to said patient intravenously at a dose between 2 and 3 mg/kg body weight/hour, preferably of 2.772 mg/kg body weight/hour, for 5 days.

According to an alternative preferred embodiment, when the CXCL8 inhibitor is R-(-)-2-(4-isobutylphenyl)propionyl methansulfonamide, it is administered to said patient orally at a dosage of 1200 mg three times a day.

The CXCL8 inhibitor compounds of the present invention may form stable pharmaceutically acceptable acid or base salts with a pharmaceutically acceptable organic or inorganic acid or base, and in such cases administration of a compound as a salt may be appropriate.

Examples of acid addition salts include acetate, adipate, ascorbate, benzoate, benzenesulfonate, bicarbonate, bisulfate, butyrate, camphorate, camphorsulfonate, choline, citrate, cyclohexyl sulfamate, diethylenediamine, ethanesulfonate, fumarate, glutamate, glycolate, hemisulfate, 2-hydroxyethylsulfonate, heptanoate, hexanoate, hydrochloride, hydrobromide, hydroiodide, hydroxymaleate, lactate, malate, maleate, methanesulfonate, meglumine, 2-naphthalenesulfonate, nitrate, oxalate, pamoate, persulfate, phenylacetate, phosphate, diphosphate, picrate, pivalate, propionate, quinate, salicylate, stearate, succinate, sulfamate, sulfanilate, sulfate, tartrate, tosylate (p-toluenesulfonate), trifluoroacetate, and undecanoate.

Examples of base addition salts include ammonium salts; alkali metal salts such as sodium, lithium and potassium salts; alkaline earth metal salts such as aluminum, calcium and magnesium salts; salts with organic bases such as dicyclohexylamine salts and N-methyl-D-glucamine; and salts with amino acids such as arginine, lysine, ornithine, and so forth. Also, basic nitrogen-containing groups may be quaternized with such agents as: lower alkyl halides, such as methyl, ethyl, propyl, and butyl halides; dialkyl sulfates such as dimethyl, diethyl, dibutyl; diamyl sulfates; long chain halides such as decyl, lauryl, myristyl and stearyl halides; arylalkyl halides such as benzyl bromide and others. Non-toxic physiologically-acceptable salts are preferred, although other salts may be useful, such as in isolating or purifying the product.

The salts may be formed by conventional means, such as by reacting the free form of the product with one or more equivalents of the appropriate acid or base in a solvent or medium in which the salt is insoluble, such as for example water or ethanol, which is removed under vacuum or by freeze drying.

The present invention also includes the prodrugs, stereoisomers, isotope-labelled, for example deuterated, derivatives and enantiomers of the CXCL8 inhibitor compounds described above.

As used herein the term "prodrug" refers to an agent, which is converted into the parent drug in vivo by some physiological chemical process (e.g., a prodrug on being brought to the physiological pH is converted to the desired drug form). Prodrugs are often useful because, in some situations, they may be easier to administer than the parent drug. For instance, they may be bioavailable by oral administration whereas the parent drug is not. The prodrug may also have improved solubility in pharmacological compositions over the parent drug. An example, without limitation, of a prodrug would be a compound of the present invention that is administered as an ester (the "prodrug") to facilitate transmittal across a cell membrane where water solubility is not beneficial, but then that it is metabolically hydrolysed once inside the cell where water solubility is beneficial.

Prodrugs have many useful properties. For example, a prodrug may be more water-soluble than the ultimate drug, thereby facilitating intravenous administration of the drug. A prodrug may also have a higher level of oral bioavailability than the ultimate drug. After administration, the prodrug is enzymatically or chemically cleaved to deliver the ultimate drug in the blood or tissue.

Ester prodrugs of the CXCL8 inhibitor compounds disclosed herein are specifically contemplated. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_1$-6 alkyl esters are particularly useful, where alkyl part of the ester has from 1 to 6 carbon atoms and includes, but is not limited to, methyl, ethyl, propyl, isopropyl, n-butyl, sec-butyl, isobutyl, t-butyl, pentyl isomers, hexyl isomers, cyclopropyl, cyclobutyl, cyclopentyl, cyclohexyl, and combinations thereof having from 1 to 6 carbon atoms.

Certain CXCL8 inhibitor compounds may exist in tautomeric forms, and this invention includes all such tautomeric forms of those compounds unless otherwise specified.

Unless otherwise stated, structures depicted herein are also meant to include all stereochemical forms of the structure; i.e., the R and S configurations for each asymmetric centre. Thus, single stereochemical isomers as well as enantiomeric and diastereomeric mixtures of the present compounds are within the scope of the invention. Thus, this invention encompasses each diastereomer or enantiomer substantially free of other isomers (>90%, and preferably >95%, free from other stereoisomers on a molar basis) as well as a mixture of such isomers.

Particular optical isomers can be obtained by resolution of the racemic mixtures according to conventional processes, e.g., by formation of diastereomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereomers by crystallization followed by liberation of the optically active bases from these salts. A different process for separation of optical isomers involves the use of a chiral chromatography column optimally chosen to maximize the separation of the enantiomers. Still another method involves synthesis of covalent diastereomers by reacting compounds of the invention with an optically pure acid in an activated form or an optically pure isocyanate. The synthesized diastereomers can be separated by conventional means such as chromatography, distillation, crystallization or sublimation, and then hydrolysed to deliver the enantiomerically pure compound. Optically active compounds of the invention can be obtained by using active starting materials. These isomers may be in the form of a free acid, a free base, an ester or a salt.

The inhibitor for use according to the first object of the invention is administered in form of a pharmaceutical composition formed by admixture of the compound admixed with one or more pharmaceutically acceptable excipients.

Typically, the CXCL8 inhibitor for use according to the first aspect of the invention is administered in the form of a pharmaceutical composition.

Accordingly, a second aspect of the present invention relates to a pharmaceutical composition comprising a CXCL8 inhibitor as above defined and at least one inert pharmaceutically acceptable excipient, for use in the treatment of patients with COVID-19 pneumonia, as above defined.

Preferably, the pharmaceutical composition of the present invention is prepared in suitable dosage forms comprising an effective amount of a CXCL8 inhibitor, a salt thereof with a pharmaceutically acceptable organic or inorganic acid or base, or a prodrug thereof, and at least one inert pharmaceutically acceptable excipient.

The administration of the pharmaceutical composition of the present invention to a patient is in accord with known methods and may comprise from one to several oral administrations per day (for example, two times a day (BID) or four times a day (QID)), parenteral administration (including intravenous, intraperitoneal, intracerebral, intrathecal, intracranial, intramuscular, intraarticular, intrasynovial, intrasternal, intraocular, intraarterial, subcutaneous, intracutaneous or intralesional injection or infusion techniques), topical, buccal and suppository administration, or by sustained release systems among other routes of administration.

Preferably, the pharmaceutical composition is for intravenous or oral administration.

In the present description and in the following claims, the wording "effective amount" means an amount of a compound or composition which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, and like factors within the knowledge and expertise of the attending physician.

As described herein, the pharmaceutical composition of the present invention comprises a CXCL8 inhibitor together with a pharmaceutically acceptable excipient, which, as used herein, includes any and all solvents, diluents, or other vehicle, dispersion or suspension aids, surface active agents, isotonic agents, thickening or emulsifying agents, preservatives, solid binders, lubricants and the like, as suited to the particular dosage form desired.

Some examples of materials which can serve as pharmaceutically acceptable excipient include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; sterilized water; Ringer's solution; buffered saline; dextrose solution; maltodextrin solution; ethyl alcohol; and phosphate buffer solutions. Moreover, the composition of the present invention may be formulated into inhalable or injectable dosage forms such as solutions, suspensions, and emulsions by further adding diluents, dispersants, and surfactants.

Further, the composition of the present invention may be suitably formulated using appropriate methods known in the art or by the method disclosed in Remington's Pharmaceutical Science (recent edition), Mack Publishing Company, Easton Pa.

The terms "pharmaceutically acceptable" and "physiologically acceptable" are intended to define, without any particular limitation, any material suitable for preparing a pharmaceutical composition to be administered to a living being.

The dosage forms can also contain other traditional ingredients such as: preservatives, stabilizers, surfactants, buffers, salts for regulating osmotic pressure, emulsifiers, sweeteners, colorants, flavourings and the like.

Also specific dosage and treatment regimens for any particular patient will depend upon a variety of factors, including for example the activity and half life of the specific compound employed, the age, body weight, general health status, sex, diet, severity and course of the disease.

The amount of a CXCL8 inhibitor or the pharmaceutically acceptable salt thereof in the pharmaceutical composition of the present invention can vary over a wide range depending on known factors, for example, the molecule used, the severity of the disease, the patient's body weight, the dosage form, the chosen route of administration, and the number of administrations per day. However, a person skilled in the art can determine the optimum amount in easily and routinely manner.

Specific dosage and treatment regimens for any particular patient will depend upon a variety of factors, including the activity of the specific compound employed, the age, body weight, general health status, sex, diet, time of administration, rate of excretion, drug combination, the severity and course of the disease, and the patient's disposition to the disease and the judgment of the treating physician.

The dosage forms of the pharmaceutical composition of the present invention can be prepared by techniques that are familiar to a pharmaceutical chemist, and comprise mixing, granulation, compression, dissolution, sterilization and the like.

In a third aspect, the present invention relates to a method of treating a patient with COVID-19 pneumonia, comprising administering to the patient a CXCL8 inhibitor as above defined.

The above method preferably comprises the steps of i) identifying a patient suffering from COVID-19 pneumonia, and ii) administering to said patient a composition comprising a CXCL8 inhibitor, a salt thereof with a pharmaceutically acceptable organic or inorganic acid or base, or a prodrug thereof.

EXAMPLES

Example 1

A phase 2 clinical study has been conducted to assess efficacy and safety of Reparixin in COVID-19 patients with severe pneumonia.

The patients participating to the trial satisfied the following inclusion criteria:

a) at least one of the following:
  - respiratory distress, RR≥30 breaths/min without oxygen;
  - Partial arterial oxygen pressure (PaO2)/Fraction of inspiration O2 (FiO2)>100<300 mmHg (1 mmHg=0.133 kPa).

b) chest imaging confirming lung involvement and inflammation.

c) inflammatory status as documented by at least one of the following: Lactate dehydrogenase (LDH)>normal range, C-reactive protein (CRP)≥100 mg/L or IL-6≥40 pg/mL, serum ferritin ≥900 ng/mL, XDP >20 mcg/mL.

All patients received a standard of care treatment, consisting in at least one of the drugs indicated in Table 1 below:

TABLE 1

| Standard of care treatment | Drug category |
|---|---|
| Remdesivir | Antiviral |
| Enoxaparin | Anti-coagulant |
| Dexamethasone | Anti-inflammatory (Corticosteroid) |
| Piperacillina + Tazobactam | Antibiotic |
| Anakinra | Anti-inflammatory (IL-1 receptor antagonist) |
| Celecoxib | Anti-Inflammatory (NSAID) |
| Paracetamol | Antipyretic |
| Warfarin | Anti-coagulant |
| Acetylsalicylic acid | Antithrombotic |
| Prednisone | Anti-inflammatory (Corticosteroid) |
| Methylprednisolone | Anti-inflammatory (Corticosteroid) |

TABLE 1-continued

| Standard of care treatment | Drug category |
|---|---|
| Prednisolone | Anti-inflammatory (Corticosteroid) |
| Dipyrone | Anti-inflammatory and analgesic |
| Azithromycin | Antibiotic |
| Ceftriaxone | Antibiotic |
| Tramadol | Analgesic |

Fourteen patients received the standard of care treatment only (Control group).

Thirty-two patients received Reparixin oral tablets 1200 mg TID in addition to the standard of care treatment (Reparixin group) for a maximum of 21 days.

In both groups, where necessary due to the presence of concomitant pathologies (diabetes, hypertension, cancer etc. . . ), the patients also continued to receive specific treatments for these.

The first occurrence of the composite primary endpoint (at least one of the following events: death, supplemental oxygen requirement, invasive mechanical ventilation use, admission to ICU, and use of a rescue medication for any reason) was evaluated in all the patients and the data obtained are shown in Table 2 below.

TABLE 2

| Time | Parameter | Reparixin (n/% patients) | Standard of care (n/% patients) | All patients (n/% of patients) |
|---|---|---|---|---|
| Baseline | Evaluable patients | 32 | 14 | 46 |
| Day 1 | Evaluable patients | 32 | 14 | 46 |
| | Composite endpoint | 3/9.4% | 8/57.1% | 11/23.9% |
| Day 2 | Evaluable patients | 27 | 6 | 33 |
| | Composite endpoint | 2/7.4% | 0 | 2/6.1% |
| Up to day 7 | Evaluable patients | 15 | 3 | 18 |
| Up to day 14 | Evaluable patients | 1 | 0 | 1 |

The data collected in the clinical trial were analyzed by means of the Kaplan-Meier methodology and the log-rank test was used to test for differences between treatment groups. The Kaplan-Meier method is a well-established method to analyse the patterns of events over time to estimate the probability of being free of event. The form of the estimated "survival curves" is a step function, with steps down occurring at those time points where there are events. As patients have events or are censored (patients who exit the analyses for other reasons than events) the number of patients remaining evaluable in the trial in each of the treatment groups is diminishing. The probabilities of being free of event are, as a consequence, estimated from fewer and fewer patients as time progresses. To give information in relation to this, the number of patients at risk at various time points are provided: these are the numbers of patients still at risk of having their first occurrence of the composite endpoint.

FIG. 1 shows the results of the analysis, wherein probability of being free from event, measured as percentage of patients free from a primary endpoint event, expressed in decimal form, is represented over time. As can be seen from the Figure, a statistically significant higher freedom from event is observed compared to the Control group, with a p-value of 0.0031 as measured by a log-rank test.

The results of the study also demonstrate that the treatment with Reparixin prevents the progression to more severe respiratory disease, as shown by the incidence of the composite endpoints as well as by the improved respiratory function among patients in the Reparixin group. The treatment with Reparixin is associated with fewer days of oxygen use and shorter subsequent duration of mechanical ventilation.

Furthermore, it has been observed that the time of recovery of patients is significantly reduced in the Reparixin group compared to the Control group.

The invention claimed is:

1. A method for treating a patient with COVID-19 viral pneumonia, the method comprising administering a CXCL8 inhibitor to the patient wherein the CXCL8 inhibitor is R-(-)-2-(4-isobutylphenyl) propionyl methansulfonamide or a pharmaceutically acceptable salt thereof.

2. The method of claim 1, wherein said inhibitor improves respiratory function in said patient, wherein said respiratory function is measured as partial arterial oxygen pressure (PaO2) to fraction of inspiration O2 (FiO2) ratio.

3. The method of claim 1, wherein said patient has a value of partial arterial oxygen pressure (PaO2) to fraction of inspiration O2 (FiO2) ratio before the treatment below 400 mmHg (wherein 1 mmHg=0.133 kPa) and/or a respiratory rate of or above 30 breaths/min without oxygen supplementation.

4. The method of claim 1, wherein said improving respiratory function comprises increasing partial arterial oxygen pressure (PaO2) to fraction of inspiration O2 (FiO2) ratio of at least 20%, 50%, 80%, 100%, 120% 150%, 200% or 250% in comparison with the ratio before treatment.

5. The method of claim 1, wherein said patient has lymphocytopenia.

6. The method of claim 4, wherein said patient is an adult patient (age of 14 years and above) and has blood concentration of lymphocytes below 1000, below 900, below 850, below 800 or below 750 cells/microliter or said patient is a child (age below 14 years) and has blood concentration of lymphocytes below 3000, below 2800, below 2500, below 2300 or below 2000 cells/microliter.

7. The method of claim 1, wherein said CXCL8 inhibitor is administered in combination with treatment with at least one drug selected from:

i) antiviral drugs;

ii) antipyretic; analgesic and antiinflammatory drugs;

iii) antibiotics; and iv) anti-coagulants and antithrombotic drugs.

8. The method of claim 1, wherein said CXCL8 inhibitor inhibits the activity of CXCL8 mediated by CXCR1 receptor or mediated by both CXCR1 and CXCR2 receptors.

9. The method of claim 1, wherein the CXCL8 inhibitor is R-(-)-2-(4-isobutylphenyl) propionyl methansulfonamide, is administered to said patient intravenously at a dose between 2 and 3 mg/kg body weight/hour for 5 days.

10. The method of claim 3, wherein the patient has a value of partial arterial oxygen pressure (PaO2) to fraction of inspiration O2 (FiO2) ratio before the treatment of between 100 and 300 mmHg.

11. The method of claim 7, wherein the antiviral drug is remdesivir.

12. The method of claim 7, wherein the drug is selected from the group consisting of dexhamethasone, paracetamol, anakinra, celecoxib, prednisone, prednisolone, methylprednisolone, piryrone, and tramadol.

13. The method of claim 7, wherein the antibiotic is selected from the group consisting of piperacillin in association with tazobactam, azithromycin, or ceftriaxone.

14. The method of claim 7, wherein the drug is selected from enoxaparin and acetylsalicylic acid.

15. The method of claim 9, wherein the CXCL8 inhibitor is the lysine salt of R-(-)-2-(4-isobutylphenyl) propionyl methansulfonamide.

16. The method of claim 9, wherein the CXCL8 inhibitor is administered to said patient intravenously at a dose of 2.772 mg/kg body weight/hour for five hours.

* * * * *